(12) United States Patent
LaVon et al.

(10) Patent No.: US 7,727,211 B2
(45) Date of Patent: *Jun. 1, 2010

(54) ABSORBENT ARTICLE HAVING A REPLACEABLE ABSORBENT CORE COMPONENT HAVING AN INSERTION POCKET

(75) Inventors: Gary Dean LaVon, Liberty Township, OH (US); Gerald Alfred Young, Lawrenceburg, IN (US); Theodora Beck, Colerain Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 302 days.

This patent is subject to a terminal disclaimer.

(21) Appl. No.: 11/143,691

(22) Filed: Jun. 2, 2005

(65) Prior Publication Data
US 2005/0228356 A1    Oct. 13, 2005

Related U.S. Application Data

(63) Continuation of application No. 09/911,108, filed on Jul. 23, 2001, now Pat. No. 6,932,800.

(51) Int. Cl.
A61F 13/15 (2006.01)
A61F 13/20 (2006.01)

(52) U.S. Cl. .................. 604/385.19; 604/386; 604/387; 604/393; 604/394; 604/395; 604/396; 604/397; 604/398; 604/399; 604/400; 604/401; 604/402; 604/385.09; 604/385.13; 604/385.14; 604/385.15; 604/385.16; 604/385.201; 604/385.23

(58) Field of Classification Search ............. 604/395, 604/385.14, 385.13, 386, 387, 393, 394, 604/396, 397, 398, 399, 400, 401, 402, 385.09, 604/385.19, 385.201, 385.23
See application file for complete search history.

(56) References Cited

U.S. PATENT DOCUMENTS

| 833,849 | A | 10/1906 | Schiff |
| 1,695,109 | A | 12/1928 | Kosloff |
| 1,893,745 | A | 1/1933 | Josias |
| 2,468,445 | A | 4/1949 | Hurst |
| 2,476,585 | A | 7/1949 | Cohen |
| 2,530,647 | A | 11/1950 | Buchler |

(Continued)

FOREIGN PATENT DOCUMENTS

CN    2073744 U    3/1991

(Continued)

OTHER PUBLICATIONS

U.S. Appl. No. 10/410,782, filed Apr. 9, 2003, All Office Actions and Responses, Apr. 9, 2003 through Oct. 17, 2007 (now U.S. Paent 7,291,137).

(Continued)

*Primary Examiner*—Tatyana Zalukaeva
*Assistant Examiner*—Ginger T Chapman
(74) *Attorney, Agent, or Firm*—William E. Gallager (57) ABSTRACT

Absorbent articles such as diapers, incontinent briefs, training pants, diaper holders and liners, and the like, designed to provide improved fit and comfort for the wearer while adequately containing body exudates. The absorbent article includes an absorbent core designed so as to retain low levels of fluid in the crotch region, relative to the other core regions, even when the core absorbs significant amounts of fluid during use. To achieve this, the absorbent core is designed such that fluid is moved substantially from the crotch region to the front and/or rear ends of the article. The absorbent core has a non-removable absorbent core component in the crotch region and removable absorbent core components in the front or rear regions of the article.

13 Claims, 7 Drawing Sheets

U.S. PATENT DOCUMENTS

| | | | |
|---|---|---|---|
| 2,574,279 A | 11/1951 | Oberle | |
| 2,688,328 A | 9/1954 | Marcus | |
| 2,695,025 A | 11/1954 | Andrews | |
| 2,788,786 A | 4/1957 | Dexter | |
| 2,790,982 A * | 5/1957 | Schneider | 401/7 |
| 2,826,199 A | 3/1958 | Brandon | |
| 2,832,346 A | 4/1958 | Morstad | |
| 2,842,129 A | 7/1958 | Ernstorff | |
| 2,868,205 A | 1/1959 | Epstein | |
| 3,050,063 A | 8/1962 | Margraf | |
| 3,162,196 A | 12/1964 | Salk | |
| RE26,151 E | 1/1967 | Duncan et al. | |
| 3,306,293 A | 2/1967 | Marder et al. | |
| 3,556,932 A | 1/1971 | Coscia et al. | |
| 3,595,235 A | 7/1971 | Jespersen | |
| 3,658,064 A | 4/1972 | Pociluyko | |
| 3,661,875 A | 5/1972 | Sieja | |
| 3,771,524 A | 11/1973 | Ralph | |
| 3,848,594 A | 11/1974 | Buell | |
| 3,860,003 A | 1/1975 | Buell | |
| 3,886,941 A | 6/1975 | Duane et al. | |
| 3,911,173 A | 10/1975 | Sprague, Jr. | |
| 3,918,433 A | 11/1975 | Fuisz | |
| 3,926,189 A | 12/1975 | Taylor | |
| 4,019,517 A | 4/1977 | Glassman | |
| 4,022,210 A | 5/1977 | Glassman | |
| 4,062,817 A | 12/1977 | Westerman | |
| 4,072,150 A | 2/1978 | Glassman | |
| 4,076,663 A | 2/1978 | Masuda et al. | |
| 4,081,301 A | 3/1978 | Buell | |
| 4,093,776 A | 6/1978 | Aoki et al. | |
| 4,257,418 A | 3/1981 | Hessner | |
| 4,260,443 A | 4/1981 | Lindsay et al. | |
| 4,265,245 A | 5/1981 | Glassman | |
| 4,326,302 A | 4/1982 | Lowe et al. | |
| 4,467,012 A | 8/1984 | Pedersen et al. | |
| 4,496,360 A | 1/1985 | Joffe et al. | |
| 4,515,595 A | 5/1985 | Kievit et al. | |
| 4,560,381 A | 12/1985 | Southwell | |
| 4,573,986 A | 3/1986 | Minetola et al. | |
| 4,578,073 A | 3/1986 | Dysart et al. | |
| 4,597,760 A | 7/1986 | Buell | |
| 4,597,761 A | 7/1986 | Buell | |
| 4,605,403 A | 8/1986 | Tucker | |
| 4,610,678 A | 9/1986 | Weisman et al. | |
| 4,615,695 A | 10/1986 | Cooper | |
| 4,625,001 A | 11/1986 | Tsubakimoto et al. | |
| 4,654,039 A | 3/1987 | Brandt et al. | |
| 4,666,983 A | 5/1987 | Tsubakimoto et al. | |
| 4,695,278 A | 9/1987 | Lawson | |
| 4,699,619 A | 10/1987 | Bernardin | |
| 4,710,188 A | 12/1987 | Runeman | |
| 4,715,918 A | 12/1987 | Lang | |
| 4,734,478 A | 3/1988 | Tsubakimoto et al. | |
| 4,756,709 A | 7/1988 | Stevens | |
| 4,770,656 A | 9/1988 | Proxmire et al. | |
| 4,773,903 A | 9/1988 | Weisman et al. | |
| D298,566 S | 11/1988 | Runeman | |
| 4,785,996 A | 11/1988 | Ziecker et al. | |
| 4,808,178 A | 2/1989 | Aziz et al. | |
| 4,816,025 A | 3/1989 | Foreman | |
| 4,822,453 A | 4/1989 | Dean et al. | |
| 4,826,499 A | 5/1989 | Ahr | |
| 4,834,736 A | 5/1989 | Boland et al. | |
| 4,834,737 A | 5/1989 | Khan | |
| 4,834,738 A | 5/1989 | Kielpikowski et al. | |
| 4,842,666 A | 6/1989 | Werenicz | |
| 4,851,069 A | 7/1989 | Packard et al. | |
| 4,872,871 A | 10/1989 | Proxmire et al. | |
| 4,888,093 A | 12/1989 | Dean et al. | |
| 4,892,598 A | 1/1990 | Stevens et al. | |
| 4,898,642 A | 2/1990 | Moore et al. | |
| 4,923,454 A | 5/1990 | Seymour et al. | |
| 4,938,756 A | 7/1990 | Salek | |
| 4,950,264 A | 8/1990 | Osborn, III | |
| 4,961,736 A | 10/1990 | McCloud | |
| 4,964,857 A | 10/1990 | Osborn | |
| 4,964,860 A | 10/1990 | Gipson et al. | |
| 4,968,312 A | 11/1990 | Khan | |
| 4,988,344 A | 1/1991 | Reising et al. | |
| 4,988,345 A | 1/1991 | Reising | |
| 4,994,037 A | 2/1991 | Bernardin | |
| 5,009,650 A | 4/1991 | Bernardin | |
| 5,009,653 A | 4/1991 | Osborn, III | |
| 5,019,068 A | 5/1991 | Perez et al. | |
| 5,061,259 A | 10/1991 | Goldman et al. | |
| 5,069,672 A | 12/1991 | Wippler et al. | |
| 5,098,423 A | 3/1992 | Pieniak et al. | |
| 5,102,597 A | 4/1992 | Roe et al. | |
| 5,108,385 A | 4/1992 | Snyder | |
| 5,128,082 A | 7/1992 | Makoui | |
| 5,137,537 A | 8/1992 | Herron et al. | |
| 5,141,505 A | 8/1992 | Barrett | |
| 5,147,345 A | 9/1992 | Young et al. | |
| 5,149,335 A | 9/1992 | Kellenberger et al. | |
| 5,167,655 A | 12/1992 | McCoy | |
| 5,176,668 A | 1/1993 | Bernardin | |
| 5,181,915 A | 1/1993 | Smith | |
| 5,188,624 A | 2/1993 | Young, Sr. et al. | |
| 5,207,662 A | 5/1993 | James | |
| 5,207,663 A | 5/1993 | McQueen | |
| 5,207,665 A | 5/1993 | Davis et al. | |
| 5,217,445 A | 6/1993 | Young et al. | |
| 5,236,428 A | 8/1993 | Zajaczkowski | |
| 5,260,345 A | 11/1993 | DesMarais et al. | |
| 5,268,224 A | 12/1993 | DesMarais et al. | |
| 5,318,554 A | 6/1994 | Young et al. | |
| 5,324,561 A | 6/1994 | Rezai et al. | |
| 5,325,543 A | 7/1994 | Allen | |
| 5,358,500 A | 10/1994 | Lavon et al. | |
| 5,360,419 A | 11/1994 | Chen et al. | |
| 5,360,422 A | 11/1994 | Brownlee et al. | |
| 5,383,867 A | 1/1995 | Klinger | |
| 5,387,207 A | 2/1995 | Dyer et al. | |
| 5,401,266 A | 3/1995 | Runeman et al. | |
| 5,405,342 A | 4/1995 | Roessler et al. | |
| 5,409,476 A | 4/1995 | Coates | |
| 5,458,591 A | 10/1995 | Roessler et al. | |
| 5,476,457 A | 12/1995 | Roessler et al. | |
| 5,486,168 A | 1/1996 | Runeman et al. | |
| 5,531,728 A | 7/1996 | Lash | |
| 5,549,589 A | 8/1996 | Horney et al. | |
| 5,550,167 A | 8/1996 | DesMarais | |
| 5,556,393 A | 9/1996 | Rönnberg | |
| 5,562,646 A | 10/1996 | Goldman et al. | |
| 5,563,179 A | 10/1996 | Stone et al. | |
| 5,569,229 A | 10/1996 | Rogers | |
| 5,599,335 A | 2/1997 | Goldman et al. | |
| 5,613,959 A * | 3/1997 | Roessler et al. | 604/364 |
| 5,636,387 A | 6/1997 | Lundy | |
| 5,650,222 A | 7/1997 | DesMarais et al. | |
| 5,667,503 A | 9/1997 | Roe et al. | |
| 5,778,110 A | 7/1998 | Furuya | |
| 5,800,416 A | 9/1998 | Seger et al. | |
| 5,817,081 A | 10/1998 | LaVon et al. | |
| 5,827,253 A | 10/1998 | Young et al. | |
| 5,843,055 A | 12/1998 | Seger | |
| 5,843,065 A | 12/1998 | Wyant | |
| 5,906,602 A | 5/1999 | Weber et al. | |
| 5,941,863 A | 8/1999 | Guidotti et al. | |
| 6,015,935 A | 1/2000 | LaVon et al. | |
| 6,083,210 A | 7/2000 | Young et al. | |
| 6,229,061 B1 | 5/2001 | Dragoo et al. | |
| 6,336,923 B1 | 1/2002 | Fujioka et al. | |

| | | |
|---|---|---|
| 6,443,933 B1 | 9/2002 | Suzuki et al. |
| 6,623,466 B1 | 9/2003 | Richardson |
| 6,689,114 B2 | 2/2004 | Bouchard et al. |
| 6,766,817 B2 | 7/2004 | de Silva |
| 6,793,649 B1 | 9/2004 | Fujioka et al. |
| 6,918,404 B2 | 7/2005 | Dias de Silva |
| 6,989,005 B1 * | 1/2006 | LaVon et al. ............ 604/385.14 |
| 6,989,006 B2 | 1/2006 | Lavon et al. |
| 7,066,586 B2 | 6/2006 | de Silva |
| 7,175,613 B2 | 2/2007 | Sugiyama et al. |
| 7,264,615 B2 | 9/2007 | Sherrod et al. |
| 7,285,255 B2 | 10/2007 | Kadlec et al. |
| 2002/0013566 A1 | 1/2002 | Chappell et al. |
| 2002/0058921 A1 | 5/2002 | Sigl |
| 2002/0112982 A1 | 8/2002 | Stagray et al. |
| 2002/0143311 A1 | 10/2002 | Brisebois |
| 2003/0199844 A1 | 10/2003 | LaVon et al. |
| 2003/0220623 A1 | 11/2003 | Sugiyama et al. |
| 2004/0024379 A1 | 2/2004 | LaVon et al. |
| 2004/0030314 A1 | 2/2004 | LaVon et al. |
| 2004/0039361 A1 | 2/2004 | LaVon et al. |

FOREIGN PATENT DOCUMENTS

| | | | |
|---|---|---|---|
| EP | 0549988 A1 * | 7/1993 | |
| EP | 0 585 766 B1 | 4/1998 | |
| EP | 0 919 213 A2 | 6/1999 | |
| GB | 493819 | 10/1938 | |
| GB | 734994 | 8/1955 | |
| GB | 1 411 087 | 10/1975 | |
| GB | 2 042 342 A | 9/1980 | |
| GB | 2 295 321 A | 5/1996 | |
| JP | 1993-86314 | 11/1993 | |
| JP | 06-121812 | 5/1994 | |
| WO | WO 89/11843 | 12/1989 | |
| WO | WO 91/10413 A1 | 7/1991 | |
| WO | WO 91/16871 A1 | 11/1991 | |
| WO | WO 92/10984 A1 | 7/1992 | |
| WO | WO 94/24973 | 11/1994 | |
| WO | WO 95/17870 A1 | 7/1995 | |
| WO | WO 98/43574 A1 * | 10/1998 | |
| WO | WO 01/60300 A1 | 8/2001 | |

OTHER PUBLICATIONS

U.S. Appl. No. 10/410,783, filed Apr. 9, 2003, All Office Actions and Responses, beginning Apr. 9, 2003.

U.S. Appl. No. 10/308,430, filed Dec. 3, 2002, All Office Actions and Responses, beginning Dec. 3, 2002.

U.S. Appl. No. 11/430,367, filed May 9, 2006, All Office Actions and Responses, beginning May 9, 2006.

U.S. Appl. No. 11/430,388, filed May 9, 2006, All Office Actions and Responses, beginning May 9, 2006.

U.S. Appl. No. 11/430,744, filed May 9, 2006, All Office Actions and Responses, beginning May 9, 2006.

U.S. Appl. No. 11/430,569, filed May 9, 2006, All Office Actions and Responses, beginning May 9, 2006.

U.S. Appl. No. 11/445,624, filed Jun. 2, 2006, All Office Actions and Responses, beginning Jun. 2, 2006.

U.S. Appl. No. 11/446,460, filed Jun. 2, 2006, All Office Actions and Responses, beginning Jun. 2, 2006.

U.S. Appl. No. 11/430,746, filed May 9, 2006, All Office Actions and Responses, beginning May 9, 2006.

U.S. Appl. No. 11/636,675, filed Dec. 11, 2006, All Office Actions and Responses, beginning Dec. 11, 2006.

U.S. Appl. No. 11/978,051, filed Oct. 29, 2007, All Office Actions and Responses beginning Oct. 29, 2007.

* cited by examiner

ABSORBENT ARTICLE HAVING A REPLACEABLE ABSORBENT CORE COMPONENT HAVING AN INSERTION POCKET

CROSS-REFERENCE TO RELATED APPLICATION

This application is a continuation of application Ser. No. 09/911,108, filed on 23 Jul. 2001, now U.S. Pat. No. 6,932,800, which is hereby incorporated in its entirety herein by reference.

FIELD OF THE INVENTION

The present invention relates to absorbent articles such as diapers, incontinent briefs, training pants, diaper holders and liners, sanitary hygiene garments, and the like, having removable and non-removable absorbent core components.

BACKGROUND OF THE INVENTION

Infants and other incontinent individuals wear absorbent articles such as diapers to absorb and retain urine and other body exudates. Absorbent articles function both to contain the discharged materials and to isolate these materials from the body of the wearer and from the wearer's garments and bed clothing. Disposable absorbent articles having many different basic designs are known in the art. For example, U.S. Pat. Re. 26,151, entitled "Disposable Diaper" describes a disposable diaper which has achieved wide acceptance and commercial success. U.S. Pat. No. 3,860,003, entitled "Contractable Side Portions For Disposable Diaper", describes an elastic leg cuff disposable diaper which has achieved wide acceptance and commercial success.

Many diaper designs are relatively wide and bulky, when dry and particularly when wet, in the region of the article that fits between the legs of the wearer. This results in a certain level of discomfort to the wearer, as these diapers tend to bunch when worn. In an effort to address wearer discomfort, U.S. Pat. No. 4,610,678 describes diapers comprising densified cores that are narrower in this region than were prior designs. Nonetheless, even these articles store significant levels of absorbed fluids in the discharge region of the article. This discharge region is positioned within the portion of the article that fits in the wearer's crotch region when worn.

Since prior absorbent articles do not effectively distribute fluid, these articles are typically designed to store significant quantities of fluid in the crotch region of the diaper. Thus, upon each loading, this region of the article becomes increasingly bulky and therefore tends to be more uncomfortable for the wearer. See, for example, U.S. Pat. No. 5,098,423, which describes a low dry bulk disposable diaper. The focus of the '423 patent is an article having a relatively low cross sectional area, when dry, particularly in the "impact zone" (defined in the patent as the second and third fifths of the article's length). Indeed, an important aspect of the described articles is the ability of the absorbent material in the impact zone to absorb fluid. The patent specifically indicates that at least 60% of the total absorbed fluid is retained in the diaper's impact zone. Thus, while the patent discusses the desire for improved fit when dry, it fails to provide an article having improved fit and comfort throughout the entire wearing period. Moreover, the primary consideration for improving fit is on thin and wide structures which fold and bunch during use, rather than optimizing narrowness and bulk, dry and wet, of the absorbent material in the crotch region. Accordingly, the articles described in the '423 patent have an overall low cross sectional area when dry, accomplished by providing a relatively thin (i.e., in the article's the z-dimension), relatively wide (i.e., in the article's x-dimension) core, with 60% of the absorbent capacity in the crotch region. This results in reduced comfort when the article is wetted with body fluid.

It therefore would be advantageous to provide an absorbent article that provides better fit and wearer comfort, even after the article is wetted with body fluids. It would be further advantageous to provide an absorbent article which has reduced bulk in the crotch region in both the dry and wet states.

SUMMARY OF THE INVENTION

The present invention provides absorbent articles designed to provide improved fit and comfort for the wearer while adequately containing body exudates. Such an absorbent article has a containment assembly (chassis) comprising an outer covering layer typically comprising a liquid pervious topsheet and a liquid impervious backsheet, and an absorbent core associated with the outer covering layer. The absorbent core is designed so as to retain low levels of fluid in the crotch region, relative to the other core regions, even when the core absorbs significant amounts of fluid during use. To achieve this, the absorbent core is designed such that fluid is moved substantially from the crotch region to the front and/or rear ends of the article, where removable absorbent core components are situated.

BRIEF DESCRIPTION OF THE DRAWINGS

While the specification concludes with claims particularly pointing out and distinctly claiming the subject matter which is regarded as forming the present invention, it is believed that the invention will be understood from the following description which is taken in conjunction with the accompanying drawings in which like designations are used to designate substantially identical elements, and in which:

DETAILED DESCRIPTION OF THE INVENTION

As used herein, the term "absorbent article" refers to devices which absorb and contain body exudates, and, more specifically, refers to devices which are placed against or in proximity to the body of the wearer to absorb and contain the various exudates discharged from the body. Absorbent articles include devices designed to absorb urine, which are used by incontinent persons. Such incontinent articles include but are not limited to diapers, adult incontinent briefs, training pants, diaper holders and liners. The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and liner.

As used herein, the term "absorbent core" refers to the portions (e.g., layers) of an absorbent article which function to acquire, distribute, transfer, store and/or redistribute fluid. Acquisition materials include materials whose primary function is to acquire then relinquish fluids. As used herein, the term "distribution material" refers to the absorbent core material(s) whose primary function is to absorb and distribute/redistribute fluid to points away from the point of initial fluid loading. As used herein, the term "storage material" refers to the absorbent core material that retains a majority of the fluid retained, on a weight basis. It should be understood that the terms "distribution material" and "storage material" are not mutually exclusive. In certain embodiments, a single material may function to provide both fluid distribution and fluid storage.

As used herein, the term "front" refers to the portion of an article or absorbent core that is intended to be positioned proximate the front of a wearer. The term "rear" refers to the portion of an article or absorbent core that is intended to be positioned proximate the back of the wearer. As such, use of the relative term "in front of" means a position in the article or core more toward the front of the article or core, while the term "behind" means a position in the article or core more toward the rear of the article or core.

As used herein, the term "z-dimension" refers to the dimension orthogonal to the length and width of the member, core or article. The z-dimension corresponds generally to the thickness of the member, core or article.

As used herein, the term "x-y dimension" refers to the plane orthogonal to the thickness of the member, core or article. The x- and y-dimensions correspond generally to the width and length, respectively, of the member, core or article.

The "crotch point" of an article and the article's absorbent core is determined by placing the article on a wearer in a standing position and then placing an extensible filament around the legs in a figure eight configuration. (See FIG. 4.) The point in the article and the absorbent core corresponding to the point of intersection of the filament is deemed to be the crotch point of the article and the absorbent core. It is understood that the crotch point is determined by placing the absorbent article on a wearer in the intended manner and determining where the crossed filament would contact the article/core.

As referred to herein, the "crotch region" of an absorbent core corresponds to 50% of the absorbent core's total length (i.e., in the y-dimension), where the crotch point is located in the longitudinal center of the crotch region. That is, the crotch region is determined by first locating the crotch point of the absorbent core, and then measuring forward and backward a distance of 25% of the core's total length.

As used herein, the term "layers" refers to identifiable components of the absorbent structure, and any structure referred to as a "layer" may actually comprise a laminate or combination of several sheets or webs of the requisite type of materials as hereinafter described. As used herein, the term "layer" includes the terms "layers" and "layered." For purposes of this invention, it should also be understood that the term "upper" refers to the layer of the absorbent core which is nearest to and faces the article topsheet; conversely, the term "lower" refers to the layer of the absorbent core which is nearest to and faces the article backsheet. It should be noted that the various members, layers, and structures of absorbent articles according to the present invention may or may not be generally planar in nature, and may be shaped or profiled in any desired configuration.

Figure 1:
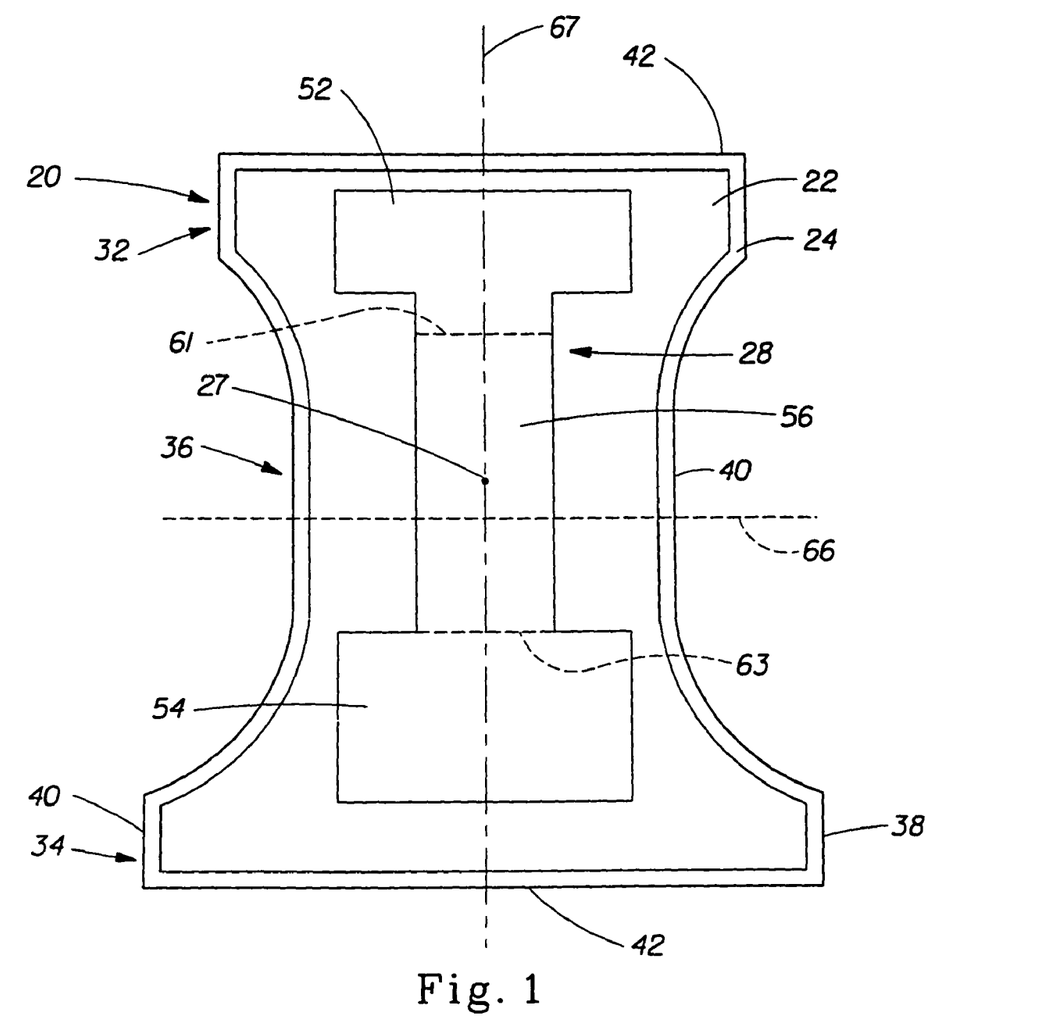
FIG. 1 is a top plan view of an absorbent article according to the present invention where the topsheet is transparent so as to more clearly show the absorbent core.

An embodiment of an absorbent article in the form of a diaper 20 having one such absorbent core according to the present invention is shown in FIG. 1. FIG. 1 is a top plan view of diaper 20 in a flat-out, uncontracted state (i.e., with any elastic-induced contraction removed) having a topsheet 22, a backsheet 24, and an absorbent core indicated generally as 28 that is positioned between topsheet 22 and backsheet 24. Topsheet 22 is shown as being transparent so as to better illustrate the absorbent core 28.

As also shown in FIG. 1, diaper 20 has a front waistband region 32, a back waistband region 34, a center region 36 and a periphery 38 that is defined by the outer edge of backsheet 24 and which has longitudinal edges designated 40 and end edges designated as 42. The longitudinal axis of diaper 20 runs essentially parallel to longitudinal edges 40 and is depicted as longitudinal centerline 67 (and corresponds to the y-direction or length), while the transverse axis runs essentially parallel to end edges 42 and is depicted as transverse centerline 66 (and corresponds to the x-direction or width). The waistband regions 32 and 34 comprise those upper portions of the diaper 20, which when worn, encircle the waist of the wearer. The center region 36 is that portion of the diaper 20 between waistband regions 32 and 34, and comprises that portion of the diaper 20 which when worn, is positioned between the legs of the wearer and covers the lower torso of the wearer. Thus, the center region 36 defines the area of typical liquid deposition for a diaper 20 or other disposable absorbent article.

Topsheet 22 and backsheet 24 can be associated together in any suitable manner. As used herein, the term "associated" encompasses configurations where topsheet 22 is directly joined to backsheet 24 by affixing the topsheet directly to the backsheet, and configurations where the topsheet is indirectly joined to the backsheet by affixing the topsheet to intermediate members which in turn are affixed to the backsheet. Preferably, the topsheet 22 and backsheet 24 are affixed directly to each other by attachment means (not shown) such as an adhesive or any other attachment means as known in the art. For example, a uniform continuous layer of adhesive, a patterned layer of adhesive, or an array of separate lines or spots of adhesive may be used to affix topsheet 22 to backsheet 24. As shown in FIG. 1, topsheet 22 has a slightly smaller size configuration than backsheet 24. However, topsheet 22 and backsheet 24 can both have the same size configuration (i.e., can be coextensive) such that they are joined together at periphery 38 of diaper 20. The size of the backsheet 24 is dictated in part by the size of the absorbent core 28 and the exact diaper design selected. In the embodiment shown in FIG. 1, the backsheet 24 has an hourglass-shaped configuration. However, other configurations such as rectangular, I-shaped, and the like are also suitable.

Although not shown, diaper 20 can have elastic members that exert a contracting force on the diaper so that it configures more closely and more comfortably to the wearer. These elastic members can be assembled in a variety of well known configurations, such as those described generally in U.S. Pat. No. 3,860,003. The elastic members can be disposed adjacent the periphery 38 of the diaper 20, preferably along each longitudinal edge 40, so that the elastic members tend to draw and hold the diaper 20 against the legs of the wearer. Alternatively, the elastic members can be disposed adjacent either or both of the end edges 42 of diaper 20 to provide a waistband as well as or rather than leg cuffs. See, for example, U.S. Pat. No. 4,515,595. The elastic members are secured to the diaper 20 in an elastically contractible condition so that in a normally unrestrained configuration, these elastic members effectively contract or gather the diaper 20. The elastic members can be secured in an elastically contractible condition in at least two ways. For example, the elastic members can be stretched and secured while the diaper 20 is in an uncontracted condition. Alternatively, the diaper 20 can be contracted, for example, by pleating, and the elastic members secured and connected to the diaper 20 while they are in their unrelaxed or unstretched condition. The elastic members can extend essentially the entire length of the diaper 20 in the center region 36, or alternatively can extend the entire length of the diaper 20, or any other length suitable to provide an elastically contractible line. The length of these elastic members is typically dictated by the diaper's design.

Referring to FIG. 1, absorbent core 28 is depicted in an "I" configuration. As is indicated above, the absorbent core will comprise front and rear regions, as well as a crotch region. These regions are defined by determining the crotch point of core 28 in accordance with the description herein. The crotch point is determined by reference to the wearer's anatomy. For purposes of illustration only, the crotch point of core 28 is depicted as item 27 in FIG. 1. Crotch point 27 is depicted as being located on the longitudinal centerline 67 of diaper 20 and absorbent core 28. This will generally be the case, regardless of the configuration of the diaper and absorbent core. However, as indicated, crotch point 27 is not located on transverse centerline 66 in this particular embodiment, though it may be in other diaper/core designs. Once the crotch point of absorbent core 28 is determined, the crotch region is determined by measuring forward from the crotch point a distance of 25% of the core's total length (depicted as transverse line 61) and backward from the crotch point a distance of 25% of the core's total length (depicted as transverse line 63). In this illustration, the crotch region is the region of the core located between transverse lines 61 and 63. As depicted in FIG. 1, absorbent core 28 is shown to have a front region 52, a back region 54, and a crotch region 56.

The topsheet 22 is compliant, soft feeling, and non-irritating to the wearer's skin. Further, the topsheet is liquid pervious permitting liquids (e.g., urine) to readily penetrate through its thickness. A suitable topsheet may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. Preferably, the topsheet is made of a hydrophobic material to isolate the wearer's skin from liquids contained in the absorbent core that is treated on at least one side with a surfactant to allow liquids to readily penetrate through its thickness.

In a preferred embodiment of the present invention, at least a portion of the topsheet is subjected to mechanical stretching in order to provide a "zero strain" stretch laminate that forms the elastic side panels. Thus, the topsheet is preferably elongatable, most preferably drawable, but not necessarily elastomeric, so that the topsheet will, upon mechanical stretching, be at least to a degree permanently elongated such that it will not fully return to its original configuration. In preferred embodiments, the topsheet can be subjected to mechanical stretching without undue rupturing or tearing of the topsheet. Thus, it is preferred that the topsheet have a low cross-machine direction (lateral direction) yield strength.

There are a number of manufacturing techniques which may be used to manufacture the topsheet. For example, the topsheet may be a nonwoven web of fibers. When the topsheet comprises a nonwoven web, the web may be spunbonded, carded, wet laid, meltblown, hydroentangled, combinations of the above, or the like. A preferred topsheet is carded and thermally bonded by means well known to those skilled in the fabrics art. A preferred topsheet comprises staple length polypropylene fibers having a denier of about 2.2. As used herein, the term "staple length fibers" refers to those fibers having a length of at least about 15.9 mm (0.625 in). Preferably, the topsheet has a basis weight from about 18 to about 25 g/m$^2$. A suitable topsheet is manufactured by Veratec, Inc., a division of International Paper Company, of Walpole, Mass., under the designation P-8.

The topsheet 22 is positioned above the body surface of the absorbent core 28. In preferred embodiments, an acquisition material (not shown) is positioned between absorbent core 28 and topsheet 22. Topsheet 22 is preferably joined thereto and to the backsheet 24 by attachment means (not shown) such as those well known in the art. Suitable attachment means are described below with respect to joining the backsheet 24 to the absorbent core 28. In a preferred embodiment of the present invention, the topsheet and the backsheet are joined directly to each other in the diaper periphery and are indirectly joined together by directly joining them to the absorbent core by the attachment means (not shown). In an alternative embodiment, the absorbent core (or the preferred acquisition material) need not be joined to either the topsheet or the backsheet such that the absorbent core is allowed to "float" between them.

The backsheet 24 is impervious to liquids (e.g., urine) and is preferably manufactured from a thin plastic film, although other flexible liquid impervious materials may also be used. As used herein, the term "flexible" refers to materials which are compliant and will readily conform to the general shape and contours of the human body. The backsheet prevents the exudates absorbed and contained in the absorbent core from wetting articles which contact the diaper such as bedsheets and undergarments. The backsheet may thus comprise a woven or nonwoven material, polymeric films such as thermoplastic films of polyethylene or polypropylene, or composite materials such as a film-coated nonwoven material. Preferably, the backsheet is a thermoplastic film having a thickness of from about 0.012 mm (0.5 mils) to about 0.051 mm (2.0 mils).

In a preferred embodiment of the present invention, at least a portion of the backsheet is subjected to mechanical stretching in order to provide both a "zero strain" stretch laminate that forms the elastic side panels and, if desired, to prestrain the portion of the backsheet coinciding with the elastic waist feature or any other elastic feature. Thus, the backsheet is preferably elongatable, most preferably drawable, but not necessarily elastomeric, so that the backsheet will, upon mechanical stretching, be at least to a degree permanently elongated such that it will not fully return to its original undistorted configuration. In preferred embodiments, the backsheet can be subjected to mechanical stretching without undue rupturing or tearing. Thus, preferred polymeric films for use as the backsheet contain a high content of linear low density polyethylene. Particularly preferred materials for the backsheet include blends comprised of about 45-90% linear low density polyethylene and about 10-55% polypropylene. Exemplary films for use as the backsheet of the present invention are manufactured by Tredegar Industries, Inc. of Terre Haute, Ind. under the designations X-8323, RR8220 blend for certain blown films, and RR5475 blend for certain cast films.

The backsheet 24 is preferably embossed (typically, to a caliper of about 0.127 mm (5.5 mils)) and/or matte finished to provide a more clothlike appearance. Further, the backsheet may permit vapors to escape from the absorbent core (i.e., may be breathable) while still preventing exudates from passing through the backsheet.

The backsheet 24 is positioned adjacent the lower surface of the absorbent core 28 and is preferably joined thereto by attachment means (not shown) such as those well known in the art. Alternatively, an additional material (e.g., acquisition material) may be placed between the backsheet 24 and the absorbent core 28. For example, the backsheet 24 may be secured to the absorbent core 28 or any intervening material by a uniform continuous layer of adhesive, a patterned layer of adhesive, or an array of separate lines, spirals, or spots of adhesive. Adhesives which have been found to be satisfactory are manufactured by Century Adhesives, Inc. of Columbus, Ohio and marketed as Century 5227; and by H. B. Fuller Company of St. Paul, Minn. and marketed as HL-1258. The attachment means will preferably comprise an open pattern network of filaments of adhesive as is disclosed in U.S. Pat. No. 4,573,986. An exemplary attachment means of an open pattern network of filaments comprises several lines of adhesive filaments swirled into a spiral pattern such as is illustrated by the apparatus and methods shown in U.S. Pat. No. 3,911,173, U.S. Pat. No. 4,785,996, and U.S. Pat. No. 4,842,666. Alternatively, the attachment means may comprise heat bonds, pressure bonds, ultrasonic bonds, dynamic mechanical bonds, or any other suitable attachment means or combinations of these attachment means as are known in the art.

Figure 2:
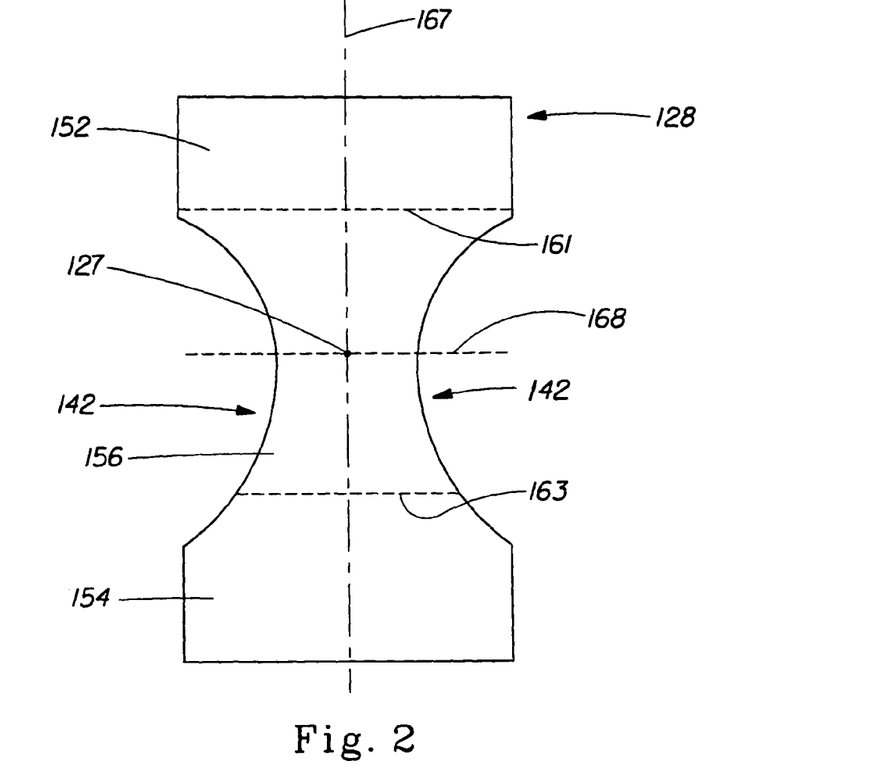
FIG. 2 is a plan view of a preferred absorbent core of the present invention.

The absorbent core 28 will comprise any absorbent means which is capable of absorbing and retaining liquids such as urine and other certain body exudates, and which is capable of providing the fluid distribution/storage properties which define the present invention. While absorbent core 28 is depicted in FIG. 1 in an "I" configuration, any shape may be utilized. For example, an absorbent core 128 is shown in FIG. 2 in an "hour glass" configuration, wherein the core has arcuate cutouts in its longitudinal edges, indicated generally as 142. For illustration purposes, the crotch point is identified by item 127. (As discussed above, the crotch point of the absorbent core is extrapolated from the wearer.) As shown, the crotch point 127 generally lies on longitudinal center line 167 and on transverse line (though not the center transverse line in this embodiment) 168. The crotch region is determined by measuring forward from the crotch point a distance of 25% of the core's total length (depicted as transverse line 161) and backward from the crotch point a distance of 25% of the core's total length (depicted as transverse line 163). The crotch region 156, is the region of the core between transverse lines 161 and 163. In addition to crotch region 156, core 128 has a front region 152 and a rear region 154.

Figure 3:
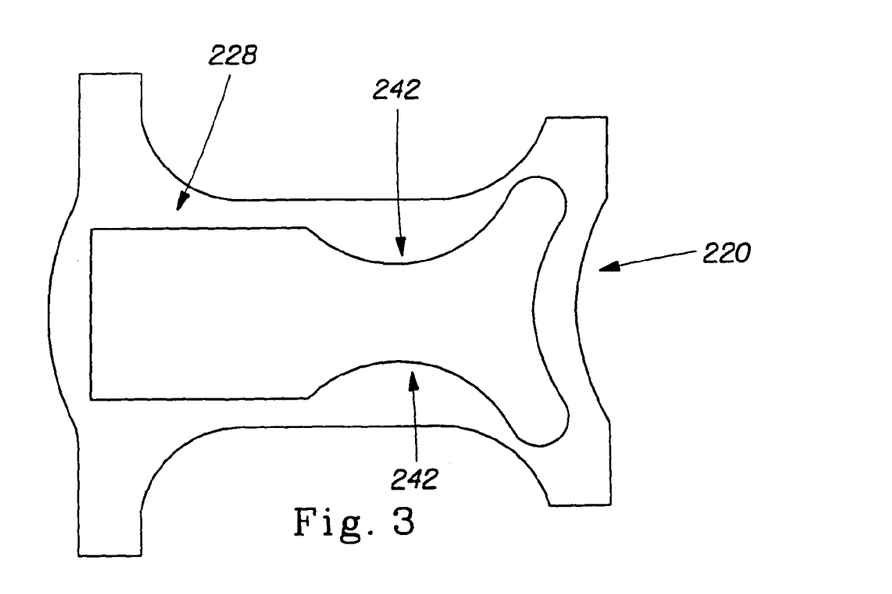
FIG. 3 is a plan view of another absorbent article of the present invention.

FIG. 3 illustrates another diaper and corresponding core configuration. In particular, diaper 220 is configured so as to fit within the low motion zone of the wearer. A disclosure of low motion articles and corresponding cores is provided in U.S. Pat. No. 5,358,500. The absorbent core, depicted generally as 228, is also configured so as to fit within the low motion zone of the wearer.

Figure 4:
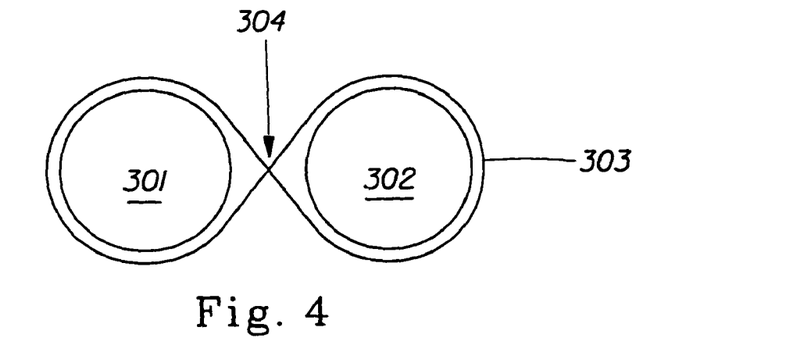
FIG. 4 illustrates how the crotch point of a wearer, an absorbent article and the corresponding absorbent core are determined.

FIG. 4 illustrates the means for determining the crotch point of an article and its absorbent core. Referring to FIG. 4, the legs of a standing wearer are depicted cross-sectionally as 301 and 302. A continuous material 303 (e.g., a string or rubber band) is twisted once and is placed around the wearer's legs at a point sufficiently close to the wearer's torso such that the intersection 304 of material 303 can be extrapolated onto the article being worn. The crotch point of the core of the article is thereby determined, and the crotch region of the core is determined per the above description.

The crotch width of the absorbent core, when dry and when wet, is also important in providing improved fit on the wearer. It is preferred that the crotch width be small, even when wetted with fluid, so that the absorbent core undergoes minimal bunching when the wearer's legs are closed. It is further preferred that at the crotch point of the absorbent core, the core have a relatively small cross sectional area (x-dimension times z-dimension).

It follows that a reduction in cross sectional area and/or crotch width of an absorbent core with a uniform capacity per unit surface area necessarily reduces the amount of material available in the zone of typical liquid deposition. Prior attempts to improve fit by reducing width in the crotch region did so by increasing capacity per unit surface area so as to maintain the necessary capacity in the crotch region. Such prior attempts utilized additional fiber in the crotch region for liquid absorption and in some instances additional hydrogel-forming polymers for liquid storage. These approaches therefore result in a negative impact on bulk both dry and wet.

In direct contrast, the present invention is based on moving the fluid deposited in the crotch region away from that region. This is reflected in a reduced level of fluid storage in the crotch region of the absorbent core. As such, the crotch region of the absorbent core will comprise material(s) that function to distribute fluids away from the crotch region. (While fluid distribution is an important function of the core's crotch region material, it is within the scope of the invention to include materials in the crotch region whose primary function is the storage of fluids, so long as the requisite properties of the present invention are achieved.) In particular, the absorbent cores of the present articles will comprise a material that exhibits high vertical wicking capacity. The ability to wick fluid vertically, i.e., fluid wicking in a direction opposite gravitational forces, is an important performance attribute since the absorbent cores are utilized in absorbent articles in a manner such that fluid to be absorbed must be moved within the article from a relatively lower position to a relatively higher position within the absorbent core of the article. This ability to move fluid against gravity is of particular import to the present invention, given that relatively small levels of fluid are to be stored in the crotch region of the core.

A preferred absorbent material for providing the requisite wicking properties is an open-celled absorbent polymeric foam material that is derived by polymerizing a High Internal Phase Water-in-Oil Emulsion (hereafter referred to a HIPE). Such polymeric foams may be formed to provide the requisite storage properties, as well as the requisite distribution properties. HIPE-derived foams which provide the requisite distribution properties for use herein are described in U.S. Pat. No. 5,650,222, U.S. Pat. No. 5,387,207, U.S. Pat. No. 5,260, 345, and U.S. Pat. No. 5,849,805. U.S. Pat. No. 5,147,345.

The distribution material suitable for use herein not only functions to distribute fluid out of the core's crotch region, but also functions to quickly acquire and preferably transport fluid, e.g., by wicking or other mechanisms, from the point of initial contact to other parts of the distribution material for eventual absorption into other core materials such as fluid storage materials. Therefore, the distribution material can also provide acquisition/distribution characteristics wherein the acquisition/distribution material is preferably polymeric foam material such as those described hereinabove that function for fluid distribution. However, the acquisition/distribution material also includes absorbent materials such as fibrous materials, fibrous non-woven materials, absorbent gelling materials, and combinations thereof.

Nonlimiting examples of fibrous materials suitable for use as a fluid acquisition/distribution material herein include, but are not limited to, the natural and synthetic fibrous materials described herein, nonlimiting specific examples of which include cellulosic fibers, modified cellulosic fibers, rayon, polyester fibers, polyethylene terephthalates, and hydrophilic nylon fibers, and mixtures thereof. Nonlimiting specific examples of absorbent gelling materials suitable for use a fluid acquisition/distribution material herein include the hydrogel-forming polymers described herein.

In those embodiments where the distribution material is not particularly suitable for storage of absorbed fluids, the absorbent core will also comprise a material, or combination of materials, whose primary function is the storage of absorbed fluids. The fluid storage material(s) acts to store body exudates away from the wearer's body so as to leave the wearer with a feeling of dryness. The storage materials are maintained in fluid contact with the distribution material(s) such that urine or other aqueous body fluids absorbed by the distribution material can be desorbed by the fluid storage material. When the storage materials are positioned in the front and/or rear regions of the absorbent core, the core provides the fit benefits by storing a majority of the absorbed fluid away from the article's crotch region.

Any material capable of desorbing the distribution material may be utilized as the storage material. For example, the storage material may comprise hydrogel-forming polymers that are water-insoluble, but water-swellable and are capable of absorbing large quantities of fluids. Such polymers are commonly referred to as "hydrocolloids" or "superabsorbent" materials. Preferred hydrogel-forming absorbent polymers for use in the present invention are disclosed in U.S. Pat. No. 3,661,875, U.S. Pat. No. 4,076,663, U.S. Pat. No. 4,093, 776, U.S. Pat. No. 4,666,983, and U.S. Pat. No. 4,734,478.

Hydrogel-forming polymers may optionally be combined with fibrous materials to form the storage material. The fibrous materials facilitate, inter alia, uptake of fluid by the hydrogel-forming polymer. Fibers useful herein include those that are naturally occurring fibers (modified or unmodified), as well as synthetically made fibers. The fibers used can be hydrophilic, hydrophobic or can be a combination of both hydrophilic and hydrophobic fibers.

For storage materials useful herein, the use of hydrophilic fibers is preferred. Suitable hydrophilic fibers for use in the present invention include cellulosic fibers, modified cellulosic fibers, rayon, polyester fibers such as polyethylene terephthalate (e.g., DACRON®), hydrophilic nylon (HYDROFIL®), and the like. For reasons of availability and cost, cellulosic fibers, in particular wood pulp fibers, are preferred for use in the present invention.

The materials utilized in the absorbent core of the present articles may be arranged in a variety of ways, so long as the requisite distribution material is included in the crotch region. As discussed above, it is preferred to have relatively little fluid storage in the crotch region. Thus, while storage materials that do not function to distribute fluid may be present in the crotch region of the absorbent core, the primary material of the crotch region will be distribution or redistribution/storage material.

Figure 5:
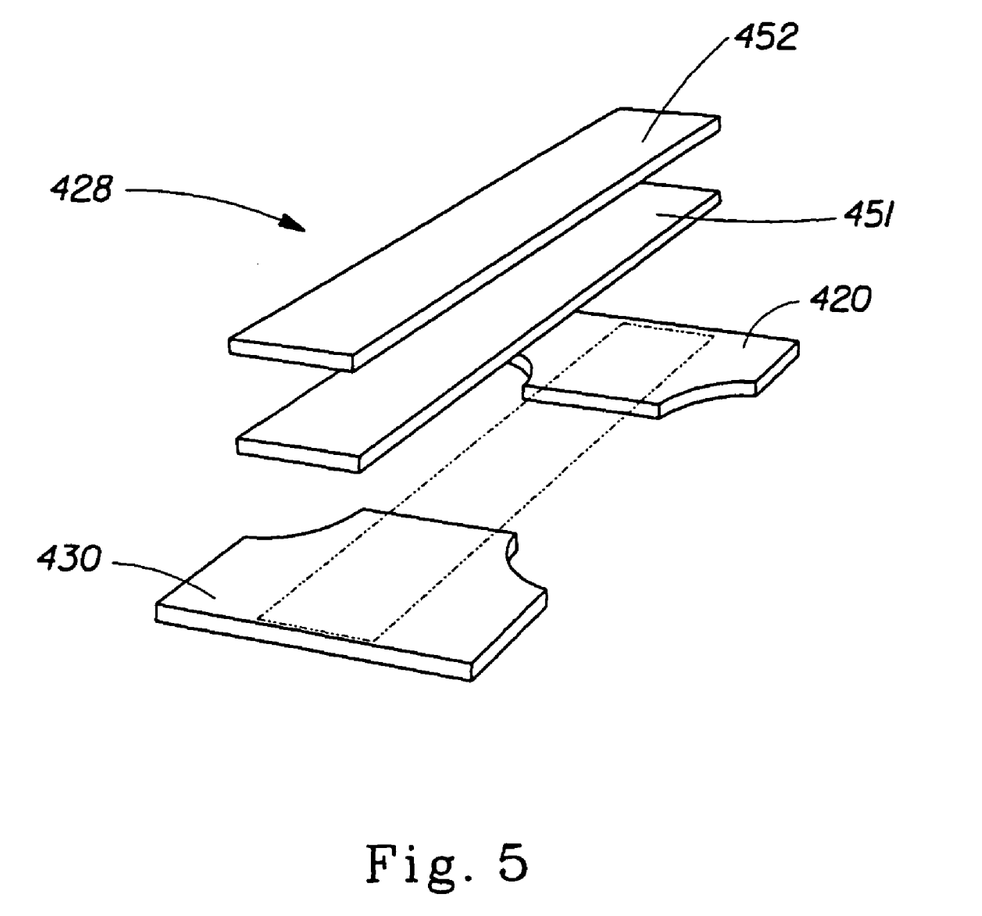
FIG. 5 is a blown apart perspective view of a multipiece absorbent core of the present invention.

The absorbent cores useful herein may comprise separate components for use in the crotch, front and rear portions of the absorbent core. FIG. 5 shows an exploded perspective view depicting the elements of an absorbent core 428. As depicted in FIG. 5, the absorbent core 428 comprises a front panel 420 and a back panel 430, both made of absorbent material, preferably material suitable for fluid storage. FIG. 5 further shows a center section 451 of absorbent material overlying the front and back panels 420 and 430, wherein the center section 451 is preferably a non-removable absorbent core component that is in fluid communication with front and back panels 420 and 430. The material of this center section 451 comprises a fluid distribution material having the vertical wicking absorbent capacities discussed above, or a material having requisite distribution and storage properties. The front panel 420 and back panel 430 are preferably removable from an absorbent article and can be replaced with similar front and back panel components. The term "removable" as used herein refers to those absorbent core components or members of the absorbent article that are intended to be removed once they become wetted and/or saturated. The term "removable" can apply to absorbent core components, absorbent core members, an insert, or other wetted and/or saturated components of the absorbent article.

Figure 6:
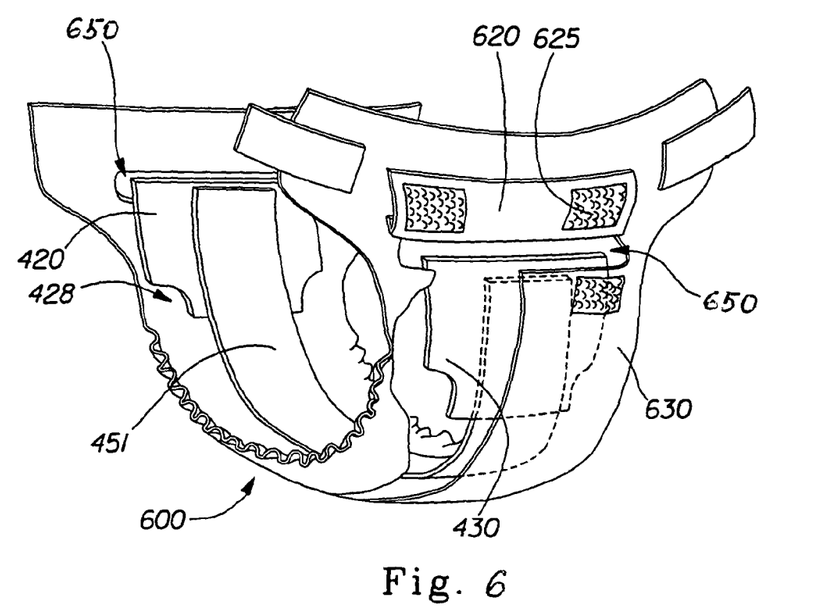
FIG. 6 is a perspective, partially segmented illustration of an absorbent article according to the present invention wherein the absorbent article comprises removable components.

The description of front panel 420 and back panel 430 are intended to be interchangeable with respect to the present invention. The front panel 420 and back panel 430 can comprise absorbent core members, absorbent core components, interface material layers, carrier layers, insertion means, removal means, disposal means, or combinations thereof. FIG. 6 shows a perspective view of absorbent core 428 comprising a removable absorbent core component such as removable back panel 430. The absorbent core 428 is shown with one layer of center section 451 and one layer of front and back panels 420 and 430. Since center section 451 and back panel 430 are discrete absorbent components, back panel 430 is removable from the absorbent article 600 through aperture 650 in backsheet 630. As shown in FIG. 6, to remove the back panel 430 flap 620 is lifted, and back panel 430 is extracted out of the absorbent article through aperture 650. Flap 620 may be secured over aperture 650 by suitable fasteners such as fasteners 625. To replace back panel 430, a fresh, dry absorbent component may be reinserted through aperture 650. In general, front panel 420, back panel 430, and corresponding apertures 650 and flaps 620 are substantially similar, but need not be. In an alternative embodiment, it may only be desired to include one aperture 650 and flap 620, for example, for access to back panel 430.

Figure 7:
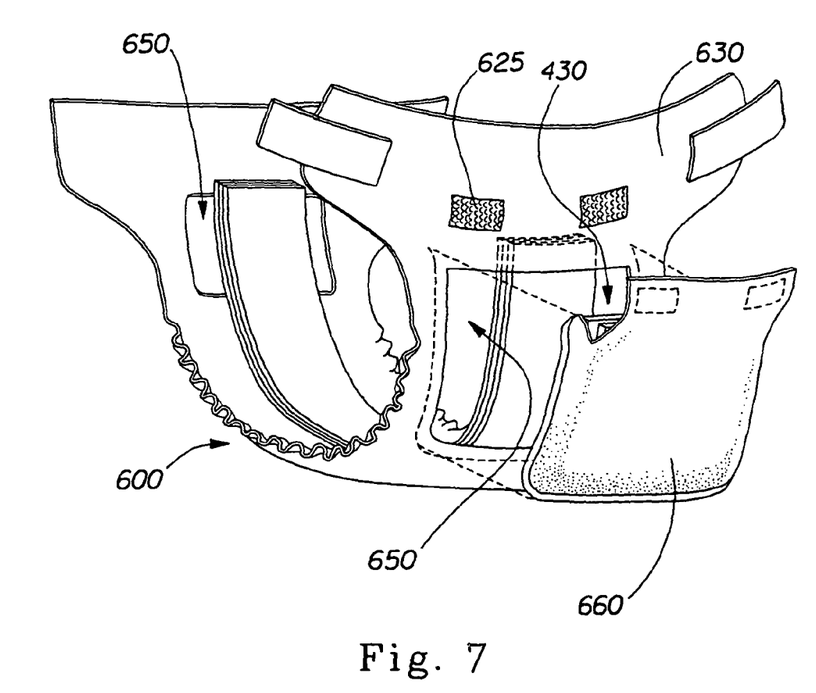
FIG. 7 is an exploded, perspective, partially segmented illustration of an absorbent article according to the present invention wherein a pocket or pouch containing removable absorbent core panel members is affixed to the absorbent article.

In a preferred embodiment as shown in FIG. 7, the absorbent article 600 has a discontinuity in the form of an aperture 650 located in the general proximity of front and rear panels 420 and 430. In this preferred embodiment a backsheet pocket 660 may be affixed adjacent aperture 650. Backsheet pocket 660 serves to contain and position front panel 420 (not shown) and back panel 430 as components made up of layered panel members, e.g., individual back panel members 680, 685, and 690 in FIG. 8. As one back panel member, e.g., back panel member 680, becomes saturated with bodily discharge it may be removed through backsheet opening 610, exposing a fresh, dry back panel member, e.g., back panel member 685. Backsheet pocket 660 is preferably resilient and pliable, and is a substantially fluid impervious barrier over aperture 650, functionally becoming an extension of backsheet 630.

Figure 8:
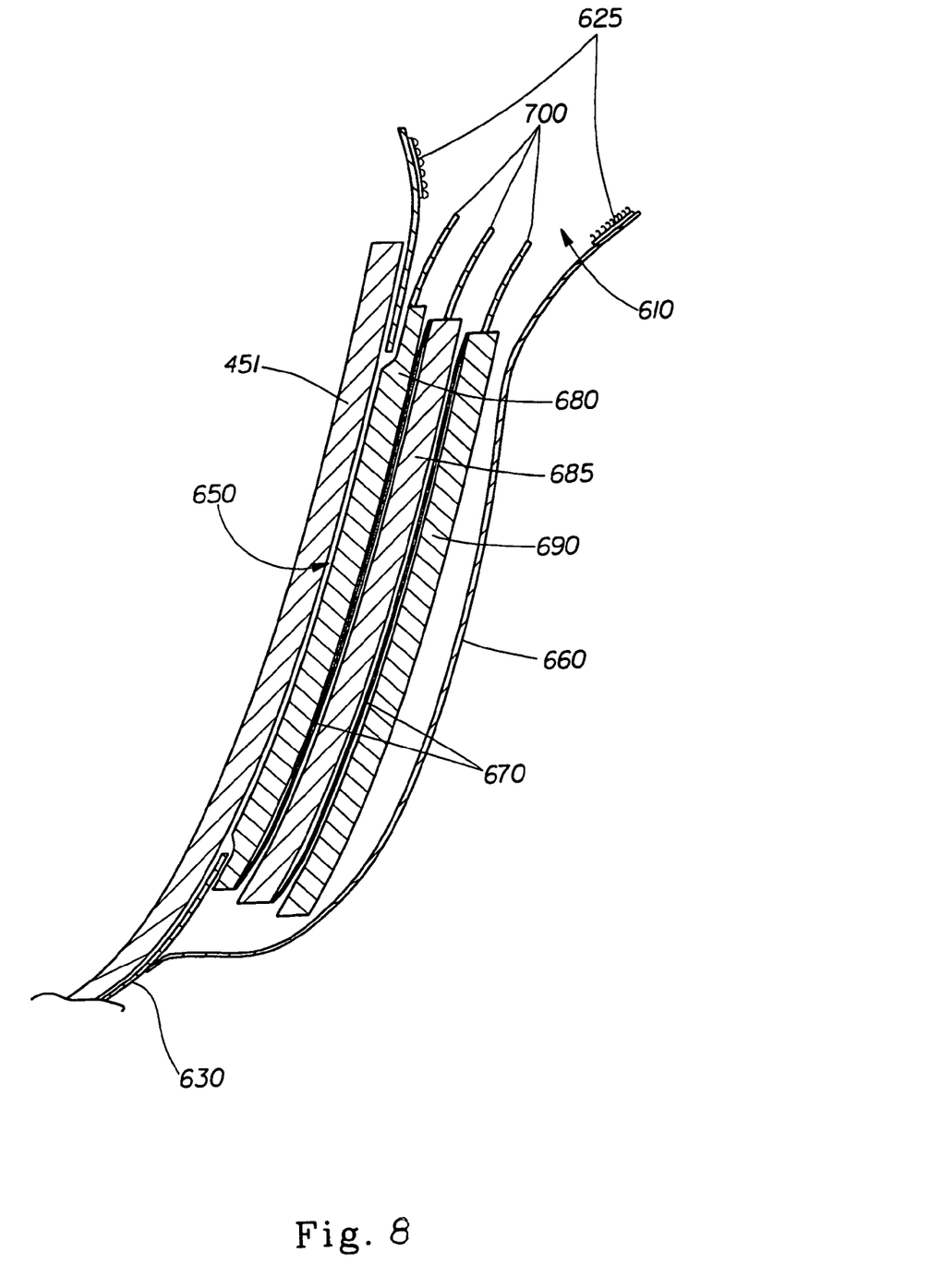
FIG. 8 is a cross-section illustration of a preferred embodiment of removable absorbent core components.

Preferably, the front panel 420 and back panel 430 comprise absorbent core panel members that are in a layered relationship and that are in fluid communication with center section 451 as shown in FIG. 8. As depicted in FIG. 8, the absorbent core panel members 680, 685, and 690 may be separated from one another by a fluid impervious blocking layer 670 so that adjacent panel members are not in fluid communication with each other, and as one panel member becomes saturated with bodily discharge it may be removed by the use of pull tabs, e.g., tabs 700, from an absorbent article thereby exposing a fresh, dry panel member for additional absorption from center section 451. The blocking layer 670 may be any fluid impervious polymer film, such as film suitable for use as a fluid impervious backsheet. The pull tabs 700 may be any type known in the art such as a strip of plastic film adhered to each panel member.

In a generally flat, unfolded state as depicted in FIG. 5, the front panel 420 and back panel 430 are separate absorbent core components positioned such that the inner front end of front panel 420 is opposed to and spaced apart from the inner back end of back panel 430. The distance between the front and back panels may be varied as necessary. In general the distance will increase as the crotch length increases with the size of the absorbent article. The length of the front panel as well as the length of the back panel may be varied independently depending on the specific design of the absorbent article and the size of the wearer for which the article is intended.

Center section 451 is preferably generally rectilinear. By "generally rectilinear" is meant that preferably the center section is of constant width along its length. In general, however, the center section 451 need only span and overlap front and back panels 420 and 430, and may have a varying width along its length. When made by the method of the present invention, center section 451 is generally rectilinear and extends from about the outer front end of front panel 420, to about the outer back end of back panel 430. In use, however, center section 451 need only be in fluid communication with front and back panels 420 and 430, preferably by overlapping in a layered relationship, and may not extend to outer front end of front panel 420 or outer back end of back panel 430.

Generally center section 451 may comprise multiple strips of absorbent material, each having individual fluid acquisition, distribution, acquisition/distribution, storage, or storage/redistribution characteristics, as well as individual shape, width, length and thickness characteristics. For example, in a preferred embodiment, a relatively thin, flexible, resilient, polymeric foam strip 451 is preferably made from the same fluid distribution/storage material as the front and back panels 420 and 430. Also depicted in FIG. 5 is an acquisition material 452 that is in fluid communication with the distribution/storage materials comprising the front and back panels 420 and 430.

In an alternate embodiment center section 451 is made from an acquisition/distribution material whereas front panel 420 and back panel 430 are made from storage/redistribution materials. Replacement of absorbent components, particularly absorbent components that are primarily suited for storage/redistribution, can result in prolonged use of an absorbent article because moisture can continue to be withdrawn away from the wearer's skin. As the storage/redistribution absorbent core components, e.g., front panel 420 and back panel 430, become saturated, they may become substantially less effective at absorbing moisture from the acquisition/distribution components of center section 451. Consequently, center section 451 becomes more saturated, thereby hindering its ability to absorb as much moisture away from the wearer's skin. However, once absorbent core components such as the front panel 420 or back panel 430 are replaced, the absorbent suction of the storage/redistribution absorbent core component is regenerated, and once again becomes capable of absorbing moisture from the acquisition/distribution components of center section 451. Therefore, the disposable absorbent article may be worn longer, and regeneration of the absorbent core may be made without removal of the article from the wearer.

As previously described, the absorbent articles useful herein comprise means to access the removable front and back panel components and to insert replaceable components, wherein these access means comprise openings or discontinuities in portions of the absorbent article such as the article's backsheet, topsheet, waist regions, or any other portion of the article, and combinations of these article components. For example, access to the removable and replaceable absorbent core components is provided through a periphery formed between the backsheet and topsheet components of the article such that access is provided by separating the topsheet and backsheet in a predetermined area of the periphery to form an opening. Removal of removable absorbent core components through the opening may be facilitated by the use of pull tabs which may be of any type known in the art such as a strip of plastic film adhered to the removable absorbent core component. Alternatively, access to the removable or replaceable absorbent core components is provided through a pocket or pouch formed between the topsheet and backsheet, or a periphery between the backsheet and other absorbent core components, or in yet another alternative embodiment through a periphery between the acquisition/distribution components and a wearer of the article. A flap having VELCRO or adhesive strips can be placed over the openings or discontinuities formed in the absorbent article to provide for fluid impermeability when the flap is closed, but allowing for multiple openings and closings to access the removable absorbent core components and insertion of replaceable components.

Figure 9:
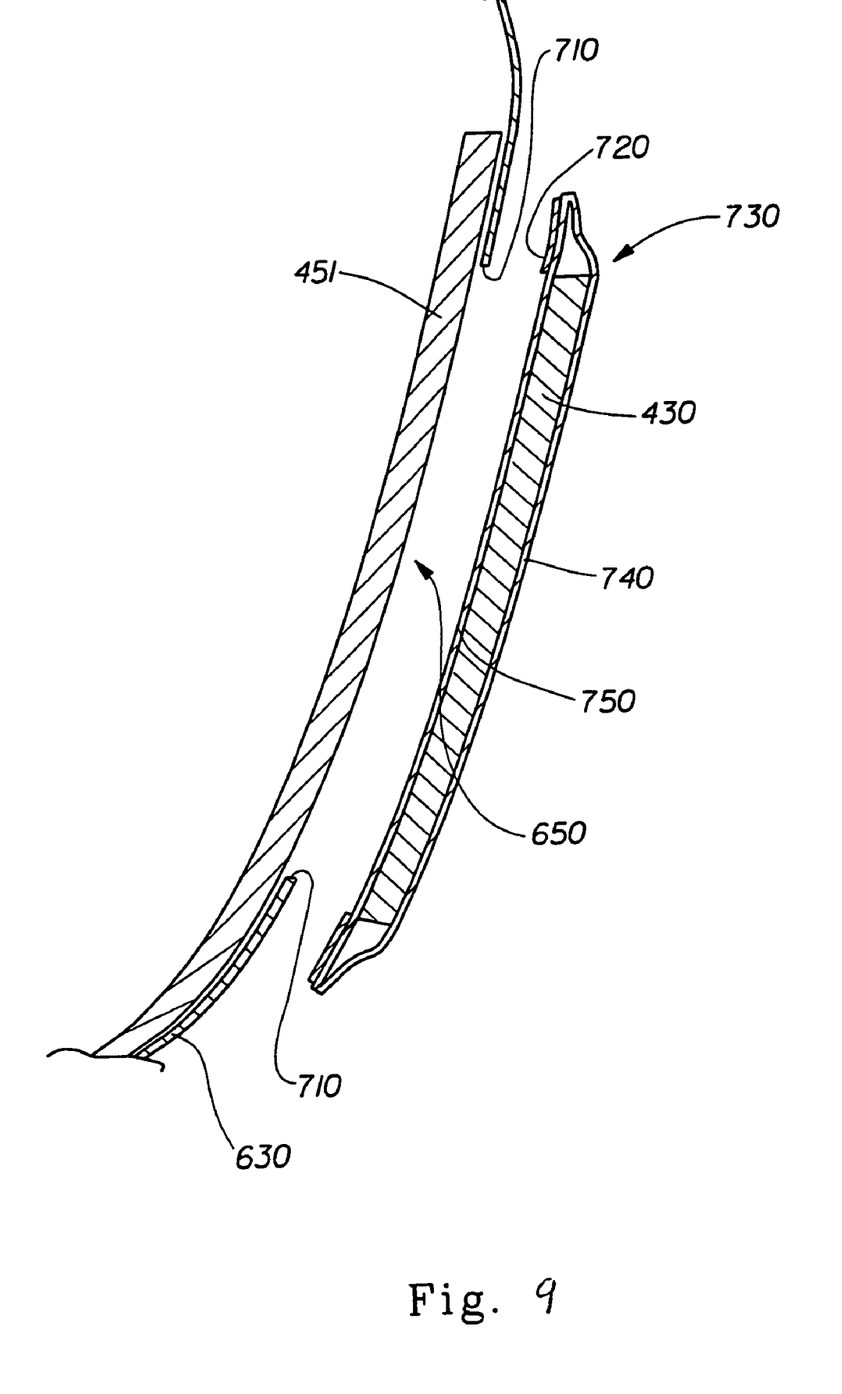
FIG. 9 is a cross-section depicting an alternative removable and replaceable absorbent core component of an absorbent article according to the present invention.

Another embodiment of access means of the removal and replacement of absorbent core components is shown in FIG. 9 wherein a back panel envelope 730 has a single back panel 430 enveloped between a substantially fluid impervious layer 740 and a substantially fluid pervious layer 750. Preferably, the back panel envelope is removably affixed, for example, to the perimeter 710 of aperture 650 using suitable adhesives 720 known in the art, so that as back panel 430 becomes saturated due to absorption of fluid from center section 451 it may be removed and replaced with a fresh, dry back panel envelope. Alternatively, the back panel envelope can have a single back panel enveloped between a substantially fluid impervious layer covering at least one side of back panel 430 and a secondary substantially fluid impervious layer which can comprise an opening for transfer of fluid from an acquisition/distribution component to back panel 430. The secondary substantially fluid impervious layer may also comprise a substantially liquid pervious transfer layer that covers the opening.

Figures 10, 11:
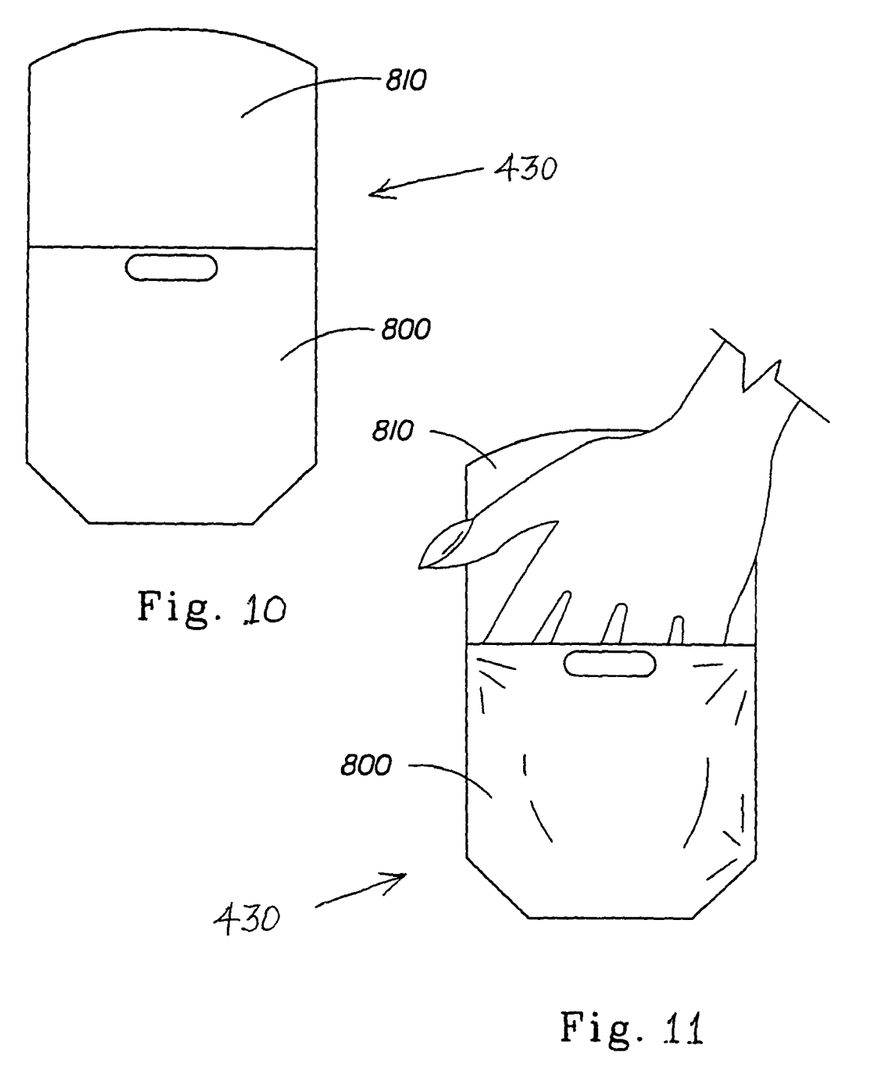
FIG. 10 is a plan view of an alternate embodiment of a removable and replaceable absorbent core component of an absorbent article according to the present invention.
FIG. 11 illustrates how the embodiment of FIG. 10 provides for removal and replacement of an absorbent core component of an absorbent article according to the present invention.

The front and back panels 420 and 430 can also be removed and replaced from an absorbent article by attaching a finger or hand insertion pocket to the front or back panel as shown in FIGS. 11 and 12. Front and back panels 420 and 430 which comprise a finger or hand insertion pocket 800 are constructed such that the insertion pocket is attached to a substantially liquid impervious outer layer 810 which covers at least one side of front panel 420 or back panel 430. The insertion pocket is attached such that it is opposite a substantially fluid pervious material such as a transfer layer that is suitable for transfer of fluid from an acquisition/distribution component to the removable storage/redistribution front panel 420 or back panel 430. The insertion pocket is designed such that the user can slip their fingers or hand into the insertion pocket with the insertion pocket either lying in the palm of their hand, or positioned on the outside of their fingers with the insertion pocket lying on top of their hand as shown in FIG. 11. In other words, the hand can be inserted into the insertion pocket palm side toward the removable absorbent core component or with the palm side of the hand away from the absorbent core component. The user can then select the orientation of their hand to complement their position relative to the wearer, for example, if they are standing behind the wearer they may choose one orientation of the insertion pocket while on the other hand if they were standing in front of the wearer reaching over or around in the case of insertion of a back panel absorbent core component, the wearer then may choose an alternative orientation of the insertion pocket.

Additionally, the position of the fluid transfer opening between the acquisition/distribution layer and the storage/redistribution material of the insertion pocket-containing front panel 420 or back panel 430 can also influence the orientation of the user's hand and the insertion pocket. The flexibility in orientation allows the user or wearer of the article to properly align the fluid transfer opening(s) in the article to the fluid transfer opening(s) on the substantially fluid pervious side of the front panel 420 or back panel 430 to ensure proper fluid transfer from the acquisition/distribution materials to the storage/redistribution materials.

The finger insertion pocket may comprise a fibrous nonwoven material, either hydrophobic or hydrophilic, a substantially liquid impermeable film material, an elastomeric film material, or combinations thereof. In an alternative embodiment, the finger insertion pocket may comprise an elastomeric material as the overall pocket or as an additional component attached to the aforementioned materials. In yet a further embodiment, the finger insertion pocket may be highly extensible allowing the insertion pocket to be extended and then wrapped over the removable or replaceable insertion pocket-containing front panel 420 or back panel 430 once the panel is removed and folded allowing for clean and easy disposal of the used insertion pocket-containing front panel 420 or back panel 430. In a different embodiment, the finger insertion pocket may be detachable along the side portions of front panel 420 or back panel 430 such that it forms a flap that can be wrapped around the end of the panel in order to cover the fluid transfer region for sanitary handling and disposal.

Statements of Incorporation by Reference and Intended Scope of Claims

The disclosures of all patents, patent applications and any patents which issue thereon, as well as any corresponding published foreign patent applications, and all publications listed and/or referenced in this description, are hereby incorporated herein by reference. It is expressly not admitted that any of the documents or any combination of the documents incorporated herein by reference teaches or discloses the present invention.

While particular embodiments and/or individual features of the present invention have been described herein, it would be obvious to those skilled in the art that various other changes and modifications can be made without departing from the spirit and scope of the invention. Further, it should be apparent that all combinations of such embodiments and features are possible and can result in preferred executions of the invention. Therefore, the appended claims are intended to cover all such changes and modifications that are within the scope of this invention.

What is claimed is:

1. A disposable diaper having a front waistband region, an opposing back waistband region, and a center region intermediate the waistband regions and comprising:
    a topsheet;
    a backsheet;
    an absorbent core disposed between the topsheet and the backsheet, the absorbent core comprising a non-removable component disposed in at least the center region and at least one replaceable component disposed in at least one of the waistband regions, the non-removable component and the removable component having respective surfaces facing each other; and
    an insertion pocket formed on the replaceable component into which a user can insert fingers to insert the replaceable component into the disposable diaper for wearing;
    wherein the diaper is adapted to provide for fluid communication between the non-removable component and the replaceable component through said facing surfaces, the open end of the insertion pocket extending generally laterally across the replaceable absorbent core component; and
    the disposable diaper is adapted to allow removal and replacement of the at least one replaceable component, and for continued use following such replacement.

2. The disposable diaper of claim 1 wherein the insertion pocket is disposed on an outer layer of the replaceable absorbent core component.

3. The disposable diaper of claim 2 wherein the outer layer is substantially liquid impervious.

4. The disposable diaper of claim 1 wherein the insertion pocket is attached along laterally opposing side portions to the replaceable absorbent core component.

5. The disposable diaper of claim 1 wherein the insertion pocket has a closed end disposed adjacent to an inner end of the replaceable absorbent core component and an opposing open end.

6. The disposable diaper of claim 5 wherein the closed end of the insertion pocket has a convergingly tapered shape.

7. The disposable diaper of claim 5 wherein the open end of the insertion pocket is substantially as wide as the replaceable absorbent core component.

8. The disposable diaper of claim 5 wherein the open end of the insertion pocket extends generally laterally across the replaceable absorbent core component.

9. The disposable diaper of claim 1 wherein the insertion pocket is smaller in length than the replaceable absorbent core component.

10. The disposable diaper of claim 9 wherein the insertion pocket is approximately half as long as the replaceable absorbent core component.

11. The disposable diaper of claim 1 wherein the insertion pocket comprises a fibrous nonwoven material.

12. The disposable diaper of claim 1 wherein the insertion pocket comprises a substantially liquid impermeable film material.

13. The disposable diaper of claim 1 wherein said adaptation to provide for fluid communication comprises a fluid pervious layer disposed between the non removable component and the replaceable component.

* * * * *